United States Patent
Wilson et al.

[19]

[11] Patent Number: 6,053,896
[45] Date of Patent: Apr. 25, 2000

[54] LEFT VENTRICLE VALVE

[75] Inventors: David W. Wilson, Erie; Kevin J. Kollar, Littleton; Thomas Joseph Wilmering, Boulder; Nicholas Scott Zeiman, Arvada; David J. Giarracco, Denver, all of Colo.

[73] Assignee: Cobe Cardiovascular Operating Co., Inc., Arvada, Colo.

[21] Appl. No.: 09/071,303

[22] Filed: May 1, 1998

[51] Int. Cl.⁷ .................................................. A61M 5/00
[52] U.S. Cl. ........................................... 604/247; 137/218
[58] Field of Search ............................. 604/301, 31, 118, 604/119, 245, 246, 247, 256, 905; 137/217, 218, 512.15, 860, 493, 493.8, 493.7

[56] References Cited

U.S. PATENT DOCUMENTS

| | | |
|---|---|---|
| D. 269,633 | 7/1983 | Willinger et al. . |
| D. 354,335 | 1/1995 | Siposs . |
| 3,285,274 | 11/1966 | Bouvier . |
| 3,324,877 | 6/1967 | Bochan . |
| 3,941,149 | 3/1976 | Mittleman . |
| 4,072,165 | 2/1978 | Bradley, Jr. ............................ 137/493 |
| 4,080,958 | 3/1978 | Bregman et al. . |
| 4,084,606 | 4/1978 | Mittleman ............................. 137/102 |
| 4,116,589 | 9/1978 | Rishton . |
| 4,237,935 | 12/1980 | Delmonte et al. ..................... 137/860 |
| 4,244,379 | 1/1981 | Smith . |
| 4,447,230 | 5/1984 | Gula et al. . |
| 4,502,502 | 3/1985 | Krug . |
| 4,549,565 | 10/1985 | Short, III ................................ 137/71 |
| 4,550,749 | 11/1985 | Krikorian . |
| 4,642,097 | 2/1987 | Siposs . |
| 4,671,786 | 6/1987 | Krug . |
| 4,675,010 | 6/1987 | Siposs et al. . |
| 4,681,571 | 7/1987 | Nehring . |
| 4,722,731 | 2/1988 | Vailancourt ............................ 604/122 |
| 4,725,266 | 2/1988 | Siposs .................................... 604/119 |
| 4,738,671 | 4/1988 | Elliott et al. . |
| 4,758,224 | 7/1988 | Siposs . |
| 4,777,951 | 10/1988 | Cribier et al. . |
| 4,919,167 | 4/1990 | Manska ................................... 137/512 |
| 5,011,469 | 4/1991 | Buckberg et al. . |
| 5,137,522 | 8/1992 | Bron ....................................... 604/247 |
| 5,169,378 | 12/1992 | Figuera . |
| 5,401,255 | 3/1995 | Sutherland et al. .................... 604/247 |
| 5,660,205 | 8/1997 | Epstein ............................... 137/512.15 |
| 5,707,356 | 1/1998 | Paul . |
| 5,860,449 | 1/1999 | Schulte ................................... 137/550 |

FOREIGN PATENT DOCUMENTS 0 452 045 B1  4/1991  European Pat. Off. .

OTHER PUBLICATIONS

Vernay Laboratories, Inc., *Single Unit Inlet and Outlet Function*, 1985 (VL–71c).

American Omni Medical, Inc., *Adjustable Suction Control Valve for Left Ventricle Venting*, 1980 (Cat. No. LV–100).

American Omni Medical, Inc., *Suction Control (Nonadustable)*, 1987 (Cat. No. RLV–2100 "B").

Advertisement, Quest Medical, Inc. *You May Not Know Our Name, But You Know Our Safety Valves*, 1993.

Bard Cardiopulmonary Division, *William Harvey® H–130 Overpressure Safety Valve Direction for Use*, Year Unknown, (R–1384/10–90/D).

*Primary Examiner*—Wynn Wood Coggins
*Assistant Examiner*—LoAn H. Thanh
*Attorney, Agent, or Firm*—Popovich & Wiles, P.A.

[57] ABSTRACT

The instant invention is directed to a left ventricle valve for use in a left ventricle drain line. The left ventricle valve includes a unidirectional check valve having duckbill valve portion and a flange portion to movably cover vacuum vent openings. The vacuum vent openings are parallel to the flow passage of the left ventricle valve. The valve also has a pressure relief opening. The invention further contemplates the valve in an extracorporeal circuit for draining the left ventricle of a heart.

28 Claims, 3 Drawing Sheets

६,०५३,८९६

LEFT VENTRICLE VALVE

FIELD OF THE INVENTION

The invention relates to pressure and vacuum relief check valves. More particularly, it relates to a left ventricle valve incorporated into a left ventricular drain line. Such drain lines may have a vacuum applied thereto for removal of blood from the left ventricle of the heart during open heart surgery. The valve of the instant invention acts both to prevent reverse blood flow to the heart, and also to prevent pressure from rising beyond a certain level in the drain line.

BACKGROUND OF THE INVENTION

During open heart surgery blood drains into the left ventricle of the heart. This may cause distention of the left ventricle, which may cause complications during open heart procedures. Therefore, it is advantageous to drain blood from the left ventricle through the use of a suction or vacuum pump and associated extracorporeal tubing. Problems associated with left ventricle drainage include the use of excessive suction, a buildup of pressure in the drain line itself, and reverse blood flow to the heart. These problems may complicate the open heart surgery.

In order to alleviate such problems arising from left ventricle drainage, extracorporeal circuits are employed both to control the amount of pressure in the drainage line and to prevent distention of the left ventricle. These circuits typically include check and relief valves, which prevent flow towards the heart, while allowing flow only away from the heart. A vent in the valve body minimizes excessive vacuum upstream from the valve. The valve allows excessive downstream pressure to be vented as well. Thus, the valve has the dual relief functions of both limiting excessive vacuum as well as controlling the amount of pressure in the downstream line.

Previously valves placed in the drainage circuit such as those in U.S. Pat. Nos. 4,671,786; 4,758,224; 4,725,266; and 4,502,502 have employed various venting and vacuum-control methods, sometimes resulting in complicated and cumbersome valves. Such valves contain several elements, including umbrella valves, duckbill valves, or a combination thereof. However, these combinations have often been elaborate, increasing the risk of failure during the operation. Complicated valve structures often lead to an increase in surface area of the flow path, which may foster a risk of undue blood coagulation in the device. This, in turn, increases the risk of occluding the valve. Furthermore, numerous and complicated venting paths also increase the risk of contamination of the blood.

In addition, the known valves are fairly expensive to produce given the intricate nature of their structure.

In order to alleviate potential pitfalls of previous valves in the art, a simpler and more reliable left ventricular relief valve that is relatively inexpensive to manufacture is needed.

SUMMARY OF THE INVENTION

It is the object of the instant invention to provide a left ventricle valve that is accurate and reliable in operation but is simple in design and easy to manufacture. It is further an object of the invention to provide a left ventricle valve that has vent passages that minimize and avoid unnecessary coagulation and further avoid and minimize foreign contamination of blood.

The present invention contemplates a left ventricle valve whose valve body has ventricular and vacuum ends for connection to a left ventricle drain line and a vacuum source respectively. The left ventricle valve of this invention includes a check valve that prevents undesirable reverse blood flow to the heart by allowing blood to flow only in a direction away from the heart.

The invention also includes vacuum vent openings in the valve body that are parallel to the direction of blood flow and the flow passage. The instant invention contemplates a check valve that has a duckbill valve portion and a bottom extension or flange that normally covers the vacuum vent openings. This bottom portion uncovers the vacuum vent openings when vacuum in the valve becomes excessive. This allows pressure from the atmosphere to enter the valve and offset any excess vacuum in the valve.

The instant invention also includes a pressure relief vent surrounded by an elastomeric sleeve situated on the valve body whereby excess pressure in the valve may be relieved.

The instant invention is further directed to an extracorporeal blood circuit where a cannula is placed in the left ventricle of the heart and blood is drawn through the cannula into a drain line, and where the blood in the drain line is conveyed from the heart, through the left ventricle valve to the vacuum source, to be drained into a cardiotomy reservoir.

DESCRIPTION OF THE PREFERRED EMBODIMENT

Figure 1:
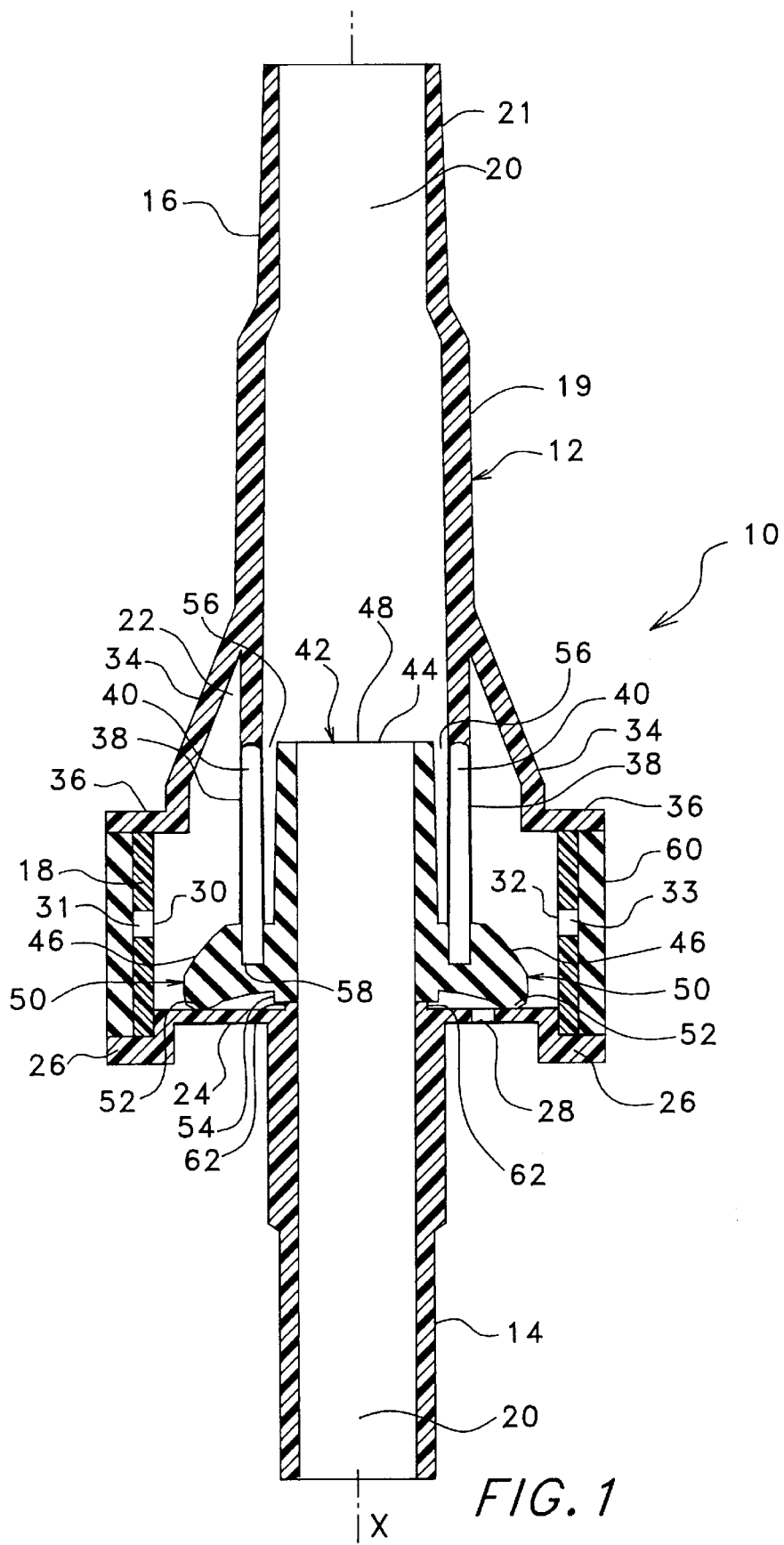
FIG. 1 is a cross-sectional view of the preferred embodiment of a left ventricle valve in accordance with the instant invention.
Figure 2:
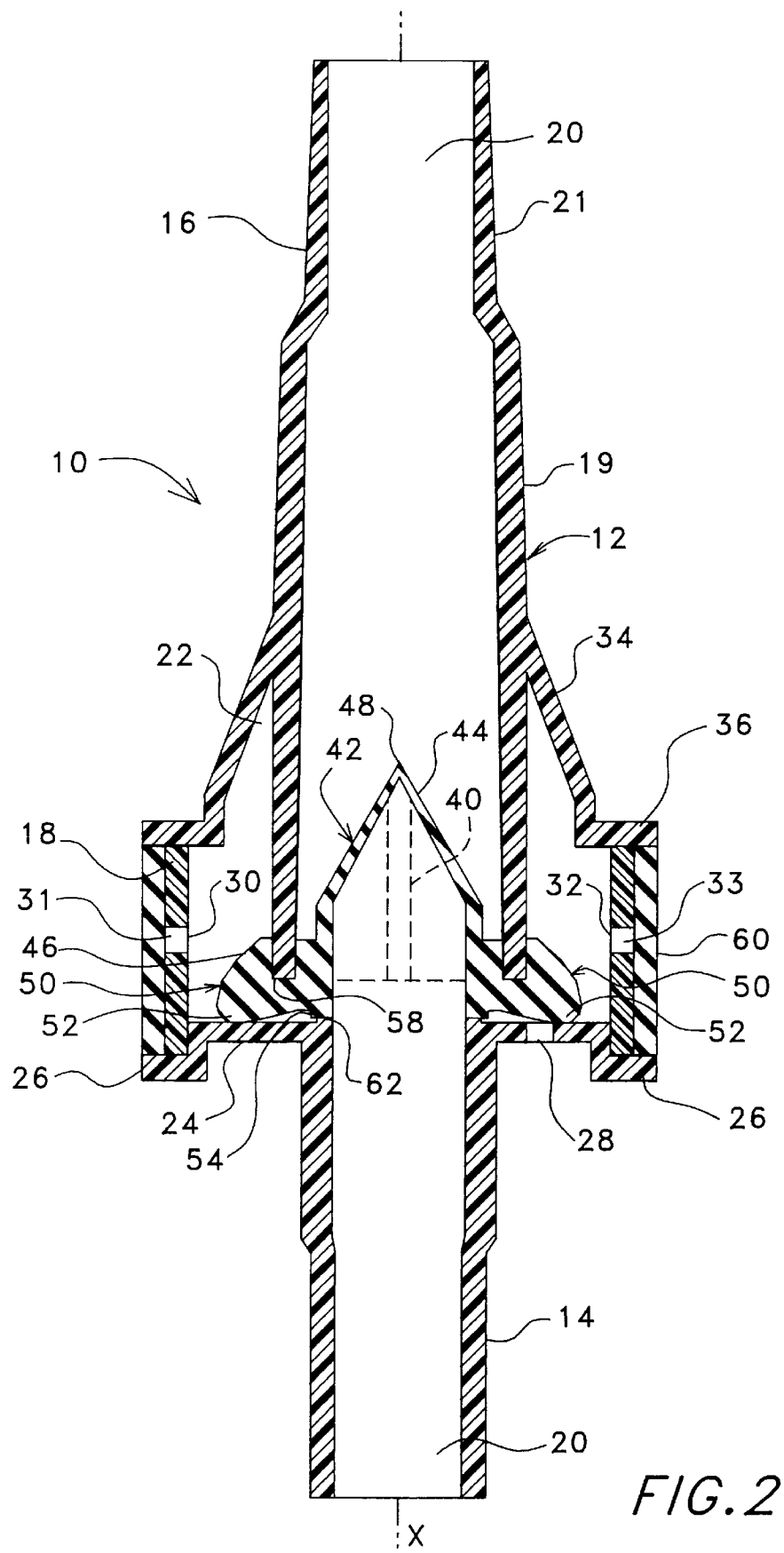
FIG. 2 is a cross-sectional view of the preferred embodiment turned ninety degrees from the orientation shown in FIG. 1.

A left ventricle valve 10 in accordance with the invention is shown in cross-section in FIGS. 1 and 2. The left ventricle valve includes a tubular body portion or valve body 12 having a first ventricular base portion 14 for connection to a left ventricular cannula and drain line, second vacuum end portion 16 for connection with a vacuum source and a main body portion 18 therebetween.

The valve body 12 encloses a flow passage 20 extending linearly from the ventricular base portion 14 through the main body portion 18 and vacuum end portion 16. The flow passage 20 includes a valve chamber 22 disposed between the main body portion 18 and the inner walls of vacuum end portion 16. The valve body 12 has a central axis X—X in line with and centered on the flow passage 20.

The ventricular base portion 14 is tapered for attachment to a drain line and includes a buttress 24 extending radially outward and a shoulder 26 for attachment to the main body portion 18, as will be described below. The buttress 24 defines vacuum vent openings 28, which are axially located and in parallel orientation to the flow passage 20. The vacuum vent openings 28 extend from the exterior of the buttress 24 into the valve chamber 22. Although only one opening is shown, it is understood that there could be any number of openings arranged around the X—X axis.

The ventricular base portion 14, as well as the vacuum end portion 16, may include optional barbs 166, 168 (FIG.

3) for maintaining a secure connection to a drain line or other extracorporeal tubing.

The main body portion 18 may be attached to the ventricular base portion 14 by gluing or other well known methods. It is also understood that the ventricular base portion 14 and the main body portion 18 can be integrally formed. The main body portion 18 includes pressure relief openings 30 and 32, defining pressure relief vents 31 and 33 in flow communication with the valve chamber 22. The pressure relief openings 30 and 32 extend from the valve chamber 22 and open to the exterior of the main body portion 18 in perpendicular orientation to flow passage 20, as is more fully described below.

The main body portion 18 may be integrally formed with the tapered vacuum end portion 16, but it is also contemplated that separate portions 16, 18 could be joined by gluing or other well known methods.

Preferably, the vacuum end portion 16 includes a first section 19 and a second section 21, which provide multiple diametric portions for accommodating tubing having nominal diameters of approximately one-quarter inch (¼") or three-eighths inch (⅜"), thereby allowing elimination of a reducer connector by users who prefer ⅜" tubing in the vacuum pump header. Specifically, the vacuum end portion sections 19, 21 are sized to have diameters slightly greater than the inside diameters of the tubing into which they will be fitted.

The vacuum end portion 16 includes a shoulder 34 extending outward toward an edge flange 36 and an inner annular ring 38. At least one slot 40 is disposed within the annular ring 38, and will be described in more detail below.

A unidirectional flow direction regulator or check valve 42 is placed along the X—X axis in valve body 12. In the preferred embodiment illustrated in FIGS. 1 and 2, the valve 42 has a duckbill valve portion 44 and a lower bottom portion 46. While the check valve 42 is shown as a duckbill type valve, it should be understood that another type of check or one directional flow valve could be used. The duckbill valve portion 44 includes an aperture 48. The bottom portion 46 includes an umbrella portion 50, which has a radial flange or extension 52. Extending radially from the check valve portion 42, the bottom portion 46 is concentric to the flow passage 20. The flange 52 further extends radially outward and rests on the buttress 24. The check valve portion 42 also includes a protrusion 54 located at the base of the bottom portion 46. The protrusion 54 is coaxial to and extends radially from the flow passage 20. A secondary flow passage 56 is defined by the inner wall of vacuum end portion 16 and the check valve portion 42.

The vacuum end portion 16, the ventricular base portion 14, and the check valve 42 are all arranged coaxially about center axis X—X to define flow passage 20. It should also be understood that the vacuum portion 16, the ventricular base portion 14, and the main body portion 18 are all preferably circular in cross-section, as shown in FIGS. 1 and 2.

In the preferred embodiment, the check valve 42 further includes a groove 58, which mates to the annular ring 38 of the vacuum end portion 16. When assembled, the check valve 42 is fitted on the upper end of the ventricular base portion 14. The annular ring 38 preloads the protrusion 54 against the buttress 24, creating a hermetic seal 62 between the bottom portion 46 with the protrusion 54 and the buttress portion 24. The annular ring 38 also preloads the radial flange portion 52 against the buttress 24.

As noted above, the annular ring 38 includes at least one slot 40, which is parallel to the flow passages 20 and 56.

Each slot 40 is in flow communication with the valve chamber 22 and the secondary flow passage 56, and operates to allow air entering through the vent opening 28 to flow into flow passage 56 from the valve chamber 22. Each slot 40 also provides a flow passage between the passages 20 and 56 and valve chamber 22 for the relief of excess pressure through the pressure relief openings 30 and 32.

The main body portion 18 is surrounded by an elastomeric sleeve 60 which normally seals the pressure relief vents 31 and 33. It is understood that the number of pressure relief vents can be varied or even a single vent can be used.

The constituents of the main body portion 18, vacuum end portion 16 and ventricular base portion 14 may be manufactured with an injection-molded opaque or transparent plastic material or may be fabricated of other known materials using known methods. The check valve 42 and elastomeric sleeve 60 may be made of a suitable elastomeric material. Examples of suitable elastomeric material include but are not limited to silicone. However, it is understood that the invention contemplates other manners of fabricating the valve portions, and that other methods and materials may be used for securing the pieces together. The only contemplated restriction for manufacture of the valve is that a provision must be made to install and secure the check valve 42 to the valve body 12. It is also contemplated that other materials may be used to manufacture the various valve components.

Figure 3:
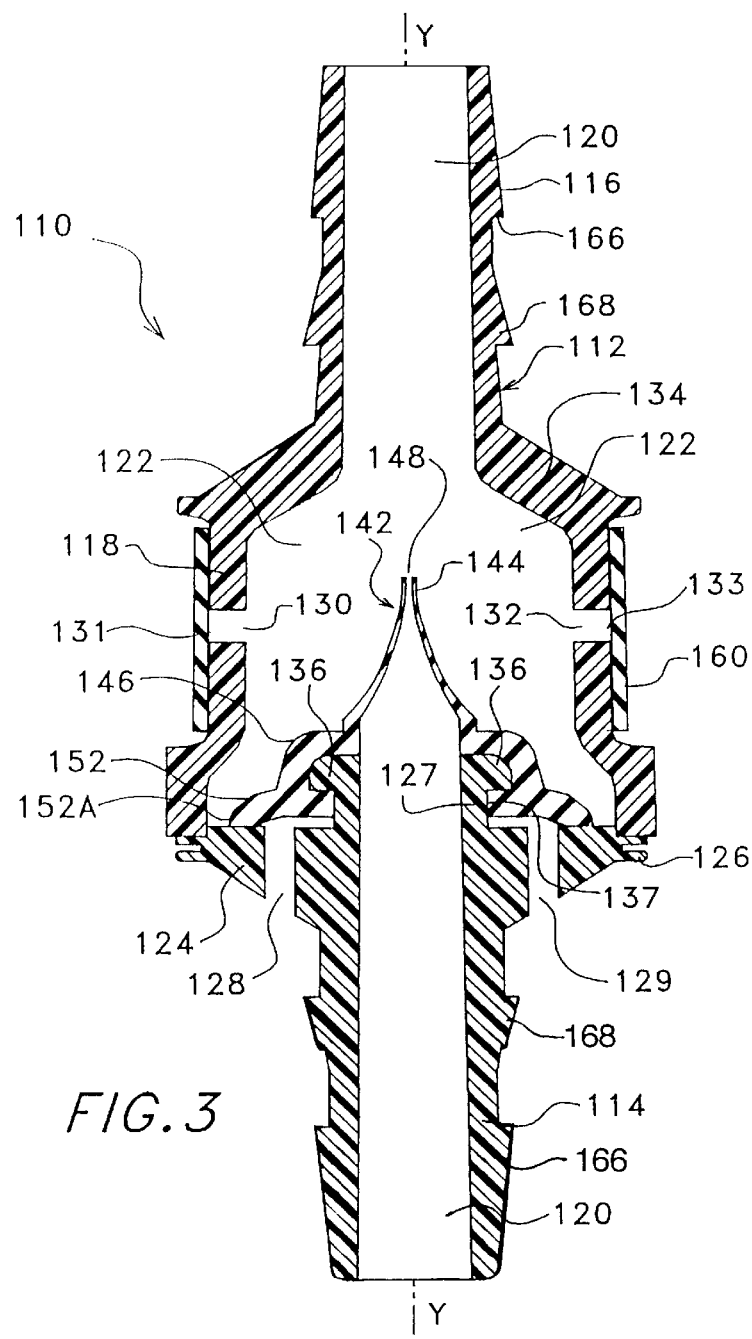
FIG. 3 is a cross-sectional view of another embodiment of a left ventricle valve of the instant invention.

Another embodiment of a left ventricle valve 110 in accordance with the invention is shown in cross-section in FIG. 3. The left ventricle valve 110 includes a tubular body portion or valve body 112 having a first ventricular base portion 114 for connection to a left ventricular cannula and drain line, a second vacuum end portion 116 for connection with a vacuum source, and a main body portion 118 therebetween.

The main body portion 118 is integrally formed with the tapered vacuum end portion 116 but it is understood that separate pieces could be formed and then joined together by gluing or other well known methods. The vacuum end portion 116 also has a shoulder 134 extending outward to an enlarged area forming the main body portion 118. The ventricular base portion 114 has a buttress 124 extending radially outward and a shoulder 126 for attachment to the main body portion 118. Again the main body portion 118 is attached to the ventricular base portion 114 by gluing or other well known methods. It is also understood the ventricular base portion 114 and main body portion 118 can be integrally formed if preferred by the construction process. The ventricular base portion 114 is also tapered for attachment to a drain line. The ventricular base portion 114, as well as the vacuum end portion 116 of the main body portion 118, include optional barbs 166 and 168 for maintaining a secure connection to a drain line or other extracorporeal tubing.

The valve body 112 encloses a flow passage 120 extending linearly from the ventricular base portion 114 through the main body portion 118 and vacuum end portion 116. The flow passage 120 includes a valve chamber 122 defined by the main body portion 118. The valve body 112 has a central axis Y—Y in line with the flow passage 120.

The main body portion 118 has pressure relief openings 130 and 132 defining pressure relief vents 131 and 133 in flow communication with the valve chamber 122. The pressure relief openings 130 and 132 of pressure relief vents 131 and 133 extend from the valve chamber 122 and open to the exterior of the main body portion 118 in perpendicular orientation to the flow passage 120.

The buttress 124 of the ventricular base portion 114 contains vacuum vent openings 128 and 129, which are axially located and in parallel orientation to the flow passage 120. The vacuum vent openings 128 and 129 extend from the exterior of the buttress 124 into the valve chamber 122. Although only two openings are shown, it is understood that there could be any number of such openings, or even only one opening arranged around the Y—Y axis.

The ventricular base portion 114 also includes a circular check valve connector 127 for attachment of a unidirectional flow regulator or check valve 142. The check valve connector 127 extends from the ventricular base portion 114 into the valve chamber 122 and surrounds the flow passage area 120 as defined by the ventricular base portion 114. The check valve connector 127 includes a concentric lip 136 extending radially outward from the Y—Y axis. The check valve connector 127 also has a recessed or indented area 137 under the lip 136 for fitting a check valve 142.

A unidirectional flow regulator or check valve 142 is placed along the Y—Y axis in the valve body 112. In the preferred embodiment the check valve 142 may be a duckbill type valve although it is understood that another type of check or one directional flow valve could be used. The check valve 142 has a duckbill valve portion 144, and includes a lower or bottom portion 146 having a radial flange or extension 152. The check valve portion 142 generally is duckbill-shaped with an aperture 148 (shown open) at the tip.

Extending radially from the check valve portion 142, the bottom portion 146 is concentric to the flow passage 120. The flange 152 further extends radially outward and rests on the buttress 124. During assembly of the left ventricle valve body 112, the check valve 142 is fitted on the circular check valve connector 127, which extends from the ventricular base portion 114 into the valve chamber 122. The bottom portion 146 and flange 152 fit around the lip 136 of the of the check valve connector 127 to grip indented or recessed area 137.

When assembled, the flange 152 normally covers the vacuum vent openings 128 and 129, which are located within the ventricular base portion 114. The vacuum vent openings 128 and 129 are located around the check valve connector 127. Additionally, the vacuum vent openings 128 and 129 extend parallel to the flow passage 120 and the flow path to allow for venting flow parallel to the flow passage 120. The flange 152 rests in the normal position in a convex shape so that a portion of the flange 152 rests on the buttress 124 and normally covers the vacuum vent openings 128 and 129.

The flange 152 is flexible for purposes of vacuum venting. FIG. 3 shows that the flange 152 is able to lift or raise from its normal position, under excessive vacuum conditions to uncover the vacuum vent openings 128 and 129 for the purposes of allowing atmospheric air to enter the valve chamber 122. The flange 152 thus acts as a reverse umbrella valve.

In this embodiment, the pressure relief vents 131, 133 are oriented perpendicularly to the flow passage 120 and extends from the interior of the main body portion 118 or the interior of the valve chamber 122 to the exterior of the valve body 112. The main body portion 118 is surrounded by an elastomeric sleeve 160 which normally seals the pressure relief vents 131 and 133. It is understood that the number of pressure relief vents can be varied or even a single vent can be used.

The constituents of the main body portion 118, vacuum end portion 116 and ventricular base portion 114 may be manufactured with a transparent or opaque injection-molded plastic material or may be fabricated of other known materials using known methods. The check valve 142 and elastomeric sleeve 160 may be made of a suitable elastomeric material. Examples of suitable elastomeric material include but are not limited to silicone. The main body portion 118 can be secured to the ventricular base portion 114 with a suitable glue for this type of application. However, it is understood that the invention contemplates other manners of fabricating the valve portions, and that other methods and materials may be used for securing the pieces together. The only contemplated restriction for manufacture of the valve is that a provision must be made to install and secure the check valve 142 to the valve body 112. It is also contemplated that other materials may be used to manufacture the various valve components.

Figure 4:
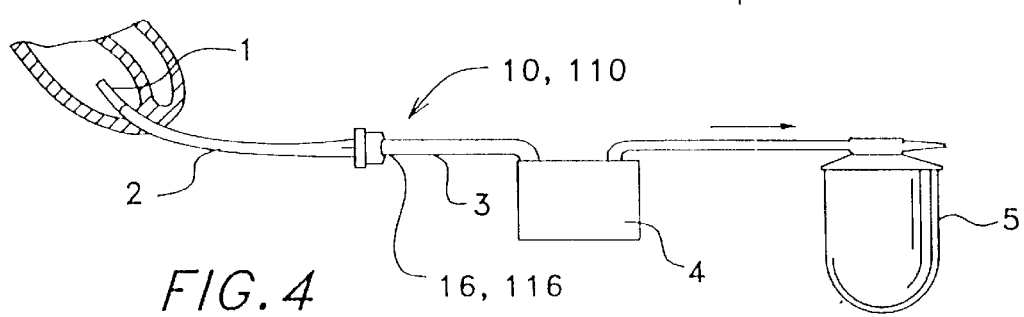
FIG. 4 is a schematic of a portion of an extracorporeal blood flow circuit including the left ventricle valve in accordance with the invention.

In use, the left ventricle valve 10, 110 as shown in FIG. 4 is incorporated into a portion of an extracorporeal blood circuit for draining blood from the left ventricle of the heart during surgery. The left ventricle valve 10, 110 is connected to a drain line 2 with an attached cannula 1 placed in the left ventricle of the heart. The valve is attached at the vacuum end portion 16, 116 or distal end to a tube 3 that is further connected to a vacuum source 4 that aids in the drainage of blood from the left ventricle. Thus blood is drawn into the cannula 1 from the heart and is conveyed through the drain line 2 and left ventricle valve 10, 110, through the tube 3 into the vacuum pump 4. Once the blood has passed through the vacuum pump, it is conveyed to a cardiotomy reservoir 5. Although a vacuum pump 4 is illustrated between the ventricle valve 10, 110 and the cardiotomy reservoir 5, it will be understood that other blood circuit configurations come within the scope of the invention, including location of the vacuum source downstream of the cardiotomy reservoir and use of a central vacuum system in lieu of a dedicated vacuum pump.

The ventricle valve will now be discussed with respect to its use in open heart surgery, with reference to the embodiment shown in FIGS. 1 and 2. During a heart procedure the vacuum pump causes blood to enter the valve body 12 via the ventricular base portion 14, flow along the flow passage 20 through flow passage 56, and exit the valve from the end of the vacuum end portion 16. The left ventricle valve 10 operates to prevent reverse blood flow to the left ventricle of the heart, therefore, blood is allowed to flow away from the heart only. Normally, blood enters the flow passage 20 through the ventricular base portion 14. Thus, given sufficient pressure, the blood then flows through the aperture 48 of the check valve 42. In this normal mode, the aperture 48 of the check valve 42 is open when blood flows with sufficient pressure through the flow passage 20 towards the main body portion 18. When such pressure is not sufficient or the flow is accidentally reversed, the reverse pressure automatically causes the aperture 48 of the check valve portion 42 to close, thus preventing reverse blood flow to the heart beyond that point.

When the left ventricle valve 10 operates for pressure relief, blood flows into flow passage 20 through the ventricular base portion 14 and into the flow passage 56 via the check valve aperture 48. Normally the blood then continues into the flow passage area 20 surrounded by the vacuum end connector portions 16 and exits into the vacuum line. However, when pressure increases in the valve chamber 22 due to an accidental reversal of blood flow, or due to other well-known causes of improper flow away from the left ventricle of the heart, the excess pressure causes the elastomeric sleeve 60 surrounding the pressure relief openings 30 and 32 to expand. This expansion uncovers the pressure relief openings 30 and 32, thus allowing the excess pressure to escape to the atmosphere.

The left ventricle valve 10 operates for vacuum venting when the pressure drops and the vacuum level in the valve chamber 22 reaches an undesirable level. When this vacuum level exceeds a certain amount, bottom portion 46 of the check valve 42, slots 40, and the vacuum vent passages 28 collaborate to reduce excess vacuum in the valve chamber 22. Under such a dangerous condition of excess vacuum, the flange 52 of the bottom portion 46 of the check valve 42 lifts upwards from the surface of the interior of the buttress 24, thus uncovering the vacuum vent opening 28 and other vacuum vent openings in the buttress 24. This allows atmospheric pressure to be conveyed through the vacuum vent openings 28 into the valve chamber 22, thus offsetting the excess vacuum in the valve chamber 22. However, any air that is incorporated in the valve chamber 22 is conveyed downstream of the check valve 42 to prevent air bubbles from entering the left ventricle via the drain line. When the vacuum level in the valve chamber 22 has been stabilized, the flange 52 of the bottom portion 46 of the check valve 42 automatically resumes its position over the vacuum vent opening 28 on the interior of the buttress 24.

Although the invention has been described with respect to a vacuum pump, it is understood that a suction pump or other well known pump could be used with the valve of the invention.

This invention is not intended to be limited to the particular embodiments disclosed in this description. It will be apparent to those skilled in the art that various modifications and variations can be made to the structure and method of the present invention without departing from the scope or spirit of the invention. In view of the foregoing, it is intended that the invention cover modifications and variations that come within the scope of the claims and their equivalents.

What is claimed is:

1. An extracorporeal flow circuit for directing a body fluid in a flow direction from a body cavity, said flow circuit comprising a cannula for insertion in the body cavity, a drain line connected to the cannula, and a vent valve placed in said drain line, said vent valve comprising:
   a valve body, said valve body having an exterior surface and an interior surface, the interior surface defining a flow passage for directing the body fluid in the flow direction, said valve body comprising a first end portion connected to said drain line, and a second end portion connectable to a vacuum or suction source;
   at least one opening in the valve body defining a vent passage for venting the flow passage, said vent passage having a first end adjacent to the interior surface of the valve body and a second end adjacent the exterior surface of the valve body, the vent passage being substantially parallel to said flow passage from the first end to the second end;
   a check valve within said valve body, said check valve comprising a valve portion allowing flow of fluid in the flow direction of the body cavity; and
   said check valve further comprising a bottom portion, said bottom portion normally covering said vent opening.

2. The circuit of claim 1 wherein said bottom portion of said check valve is movable to uncover said vent passage when pressure in the flow passage falls below a predetermined amount.

3. The circuit of claim 2 further comprising at least one side pressure relief opening in the valve body of said vent valve for controlling pressure within said flow passage.

4. The circuit of claim 3 further comprising a flexible sleeve normally covering the pressure relief opening wherein when pressure in said flow passage exceeds a certain level said flexible sleeve uncovers said pressure relief opening to allow excess pressure within the flow passage to escape through the pressure relief opening, and when pressure in said flow passage falls below a certain level said flexible sleeve seals the pressure relief opening.

5. The circuit of claim 2 wherein said valve portion of said check valve is a one directional duckbill valve.

6. The circuit of claim 2 wherein said bottom portion of said check valve comprises a radial flange extending from said valve portion of said check valve, said flange normally covering the vent passage.

7. The circuit of claim 2 wherein said check valve prevents flow of body fluid in a direction opposite the flow direction from the body cavity.

8. The circuit of claim 2 further comprising a ;lurality of vent passages in the valve body wherein said bottom portion of the check valve normally covers the plurality of vent passages.

9. The circuit of claim 1 wherein said valve body further comprises at least one side pressure relief opening for controlling pressure within said flow passage.

10. The circuit of claim 9 further comprising a flexible sleeve normally covering the pressure relief opening wherein when pressure in said flow passage exceeds a certain level said flexible sleeve uncovers said pressure relief opening to allow excess pressure within the flow passage to escape through the pressure relief opening, and when pressure in said flow passage falls below a certain level said flexible sleeve seals the pressure relief opening.

11. The circuit of claim 1 wherein said valve includes a grooved portion and wherein said second end portion includes an annular ring portion, said annular ring portion matingly engagable with said grooved portion.

12. The circuit of claim 11 further comprising at least one slot disposed in said annular ring portion, said slot parallel to and in flow communication with said flow passage.

13. The circuit of claim 1 wherein said second end portion comprises a first section and a second section, said first section having a diameter greater than that of said second section.

14. A left ventricle valve for use in a flow circuit to drain the left ventricle of a heart, said left ventricle valve comprising:
   a valve body, said valve body having an exterior surface and an interior surface, the interior surface defining a flow passage for directing fluid from the left ventricle in a flow direction, said valve body having a first ventricular end, and a second end connectable to a vacuum or suction source;
   at least one opening in the valve body defining a vent passage for venting the flow passage, said vent passage having a first end adjacent to the interior surface of the valve body and a second end adjacent the exterior surface of the valve body, the vent passage being substantially parallel to said flow passage from the first end to the second end;
   a check valve within said valve body, said check valve comprising a valve portion allowing flow of fluid in the flow from said first ventricular end to said second end; and
   said check valve further comprising a bottom portion, said bottom portion normally covering said vent opening.

15. The left ventricle valve of claim 14 wherein the bottom portion of said check valve is movable to uncover said vent passage when pressure in said flow passage falls below a predetermined value.

16. The left ventricle valve of claim 15 wherein said valve includes a grooved portion.

17. The left ventricle valve of claim 16 wherein said second end includes an annular ring portion, said annular ring portion matingly engagable with said grooved portion.

18. The left ventricle valve of claim 15 further comprising at least one side pressure relief opening in the valve body of said ventricle valve for controlling pressure within said flow passage.

19. The left ventricle valve of claim 18 further comprising a flexible sleeve surrounding the pressure relief opening wherein when pressure in said flow passage exceeds a certain level said flexible sleeve allows pressure to escape through the pressure relief opening, and when pressure in said flow passage falls below a certain level said flexible sleeve seals the pressure relief opening.

20. The left ventricle valve of claim 15 wherein said check valve prevents flow of fluid in a direction opposite the flow direction from the left ventricle.

21. The left ventricle valve of claim 15 further comprising a plurality of vent passages in the valve body wherein said bottom portion of said check valve normally covers the plurality of vent passages.

22. The left ventricle valve of claim 15 wherein said bottom portion of said check valve comprises a radial flange extending from said valve portion, said flange normally covering the vent passage.

23. The left ventricle valve of claim 15 wherein said valve portion of said check valve is a one directional duckbill valve.

24. The left ventricle valve of claim 14 further comprising at least one side pressure relief opening in the body portion of said ventricle valve for controlling pressure within said flow passage.

25. The left ventricle valve of claim 24 further comprising a flexible sleeve surrounding the pressure relief opening wherein when pressure in said flow passage exceeds a certain level said flexible sleeve allows pressure to escape through the pressure relief opening, and when pressure in said flow passage falls below a certain level said flexible sleeve seals the pressure relief opening.

26. The left ventricle valve of claim 14 wherein said check valve consists of an elastomeric material.

27. The left ventricle valve of claim 14 wherein said second end portion comprises a first section and a second section, said first section having a diameter greater than that of said second section.

28. A left ventricle valve for use in a flow circuit to drain the left ventricle of a heart, said left ventricle valve comprising:

a body portion, said body portion defining a flow passage for directing fluid from the left ventricle in a flow direction, said body portion having a first ventricular end, and a second end connectable to a vacuum or suction source;

at least one opening in the body portion defining a vent opening for venting the body portion, said vent opening being substantially parallel to said flow passage;

a check valve within said body, said check valve comprising a valve portion allowing flow of fluid in the flow from said first ventricular end to said second end and a bottom portion, said bottom portion normally covering said vent opening, wherein said bottom portion is movable to uncover said vent opening when pressure in said flow passage falls below a predetermined value;

wherein said ventricle valve comprises a grooved portion and said second end includes an annular ring portion matingly engagable with said grooved portion; and wherein said ventricle valve further comprises at least one slot disposed in said annular ring portion, said slot parallel to and in flow communication with said flow passage.

* * * * *